United States Patent [19]

Liu

[11] Patent Number: 4,568,429

[45] Date of Patent: Feb. 4, 1986

[54] PROCESS FOR THE PREPARATION OF 2,4-DIHYDROXYBENZOPHENONES

[75] Inventor: Kou-Chang Liu, Wayne, N.J.

[73] Assignee: GAF Corporation, Wayne, N.J.

[21] Appl. No.: 585,713

[22] Filed: Mar. 2, 1984

[51] Int. Cl.$^4$ .............................................. B01D 3/10
[52] U.S. Cl. ...................................... 203/91; 203/38; 203/58; 203/47; 568/315; 568/322; 568/324
[58] Field of Search ...................... 203/91, 50, 28, 57, 203/58, 47, 38; 568/322, 324, 315

[56] References Cited

U.S. PATENT DOCUMENTS

| | | | |
|---|---|---|---|
| 2,682,559 | 6/1954 | Stanley et al. | 568/324 |
| 2,861,104 | 11/1958 | Von Glahn | 568/322 |
| 3,526,666 | 9/1970 | Ponder | 568/315 |
| 3,830,845 | 8/1974 | Arimoto et al. | 568/324 |
| 3,843,729 | 10/1974 | Lachmann et al. | 568/322 |
| 3,850,988 | 11/1974 | Ruby | 568/324 |

FOREIGN PATENT DOCUMENTS

| | | | |
|---|---|---|---|
| 1246958 | 9/1971 | United Kingdom | 568/322 |
| 1430519 | 3/1976 | United Kingdom | 568/324 |

OTHER PUBLICATIONS

Chemical Abstract, vol. 83, 1975, Hireaki et al., "2-Hydroxy-4-(Alkadienyloxy)benzophenones", Abstract No. 78868x, p. 628.

*Primary Examiner*—S. Leon Bashore
*Assistant Examiner*—V. Manoharan
*Attorney, Agent, or Firm*—Marilyn J. Maue; Joshua J. Ward

[57] ABSTRACT

2,4-Dihydroxybenzophenone is prepared substantially quantitatively and in a highly purified form by reacting resorcinol with a benzotrihalide in the presence of an aqueous solution of N-methylpyrrolidone and subsequently subjecting the crude reaction product mixture to vacuum distillation.

13 Claims, No Drawings

PROCESS FOR THE PREPARATION OF 2,4-DIHYDROXYBENZOPHENONES

The present invention relates to a process involving the use of an aqueous N-methylpyrrolidone reaction media and product purification by vacuum distillation in the preparation of 2,4-dihydroxybenzophenone from a resorcinol and a benzoic coreactant, particularly a benzotrihalide. In one aspect, the process resides in vacuum distillation of the crude reaction product mixture, and, in another aspect, the invention relates to the use of an aqueous solution of N-methylpyrrolidone as the solvent media for the reaction.

PRIOR ART

Heretofore 2,4-dihydroxybenzophenone has been prepared by reacting resorcinol with benzoyl chloride or benzoic acid under anhydrous conditions in the presence of Friedel-Crafts catalysts such as $AlCl_3$ or $ZnCl_2$. These processes have resulted in relatively low yields of product. The process is also inefficient since the moisture absorptive catalyst is consumed in an amount of at least 1 mole/mole of benzoic reactant. This, coupled with the low yield, creates serious waste disposal problems.

Various improvements for prior processes have been proposed to improve conversion to product. One such improvement involves the use of a lower alcohol or lower fatty acid solvent for the reaction between resorcinol and benzotrichloride, followed by decolorization with an active clay (U.S. Pat. No. 3,769,349). While this process succeeds in improving resorcinol conversion, the product generally contains a substantial quantity of impurities particularly reddish brown resorcinolbenzein colorant. Also, the patented process involving benzotrichloride requires complicated purification and recovery steps including adjustment of the pH to about 7, and treatment with a solid decolorizing agent followed by azeotropic dehydration and finally crystallization. In spite of the use of clay decolorizers, the product does not achieve expectations since the clay is incapable of completely removing highly colored impurities. It is apparent that the recovery of product by this improved process is both time consuming and economically unsatisfactory. Additionally, the use of certain solvents, such as carcinogenic dioxane, require special handling which greatly adds to the expense of the process.

It is therefore an object of the present invention to overcome the disadvantages enumerated above.

Another object of the invention is to provide an improved and commercially feasible process for the preparation of 2,4-dihydroxybenzophenone in high yield.

Still another object of the invention is to provide for direct and economic recovery of 2,4-dihydroxybenzophenone in a more purified state from a crude reaction mixture.

Yet another object is to provide an economical process for the purification of arylphenones when produced by any method which coproduces impurities and colorants difficult to remove by conventional methods.

These and other objects of the invention will become apparent from the following description and disclosure.

THE INVENTION

According to this invention the crude product of the reaction between a resorcinol and a benzoic coreactant to produce a dihydroxybenzophenone is subjected to vacuum distillation under a pressure not exceeding 160 mm Hg and at a critical temperature between 120° C. and about 350° C.

Most particularly, in a process involving the reaction of resorcinol with a benzotrihalide to produce 2,4-dihydroxybenzophenone, the use of an aqueous N-methylpyrrolidone solvent solution of between about 10 and about 90, preferably between about 20 and about 50 wt. % N-methylpyrrolidone concentration and subsequent vacuum distillation of the crude product at a temperature of from 150° C. to about 250° C. under between about 0.001 to 60 mm Hg, minimizes the formation of undesirable by products and eliminates the presence of color bodies and other impurities from the product while realizing conversion to product in at least 90% yield. Product, having a high melting point (about 145° C.) obtainable by this process, is recovered as solid white crystals.

The use of vacuum distillation for recovery of 2,4-dihydroxybenzophenone or a derivative thereof produces a reaction mixture in which the product is obtained as a solid and the impurities contained in the crude mixture are also in solid form. Generally, in situations which involve solid products contaminated with solid impurities, the conventional purification involves successive crystallizations, liquid washing and extraction and/or treatment with an active clay. In the present invention however, it is found that by melting the solids and conducting the distillation under a critical temperature and vacuum, the impurities associated with product are effectively and economically removed and product is obtained in a highly purified state. Moreover, no coloration of the product develops on standing or storage for extended periods, thus, indicating high color stability. Additionally, the vacuum distillation purification of product eliminates the need for decolorizing agents and time consuming extraction and recrystallization steps required in prior processes which produce unsatisfactory results.

Another advantage of the present invention over certain solvents proposed heretofore for the reaction of resorcinol and a benzotrihalide is the use of aqueous N-methylpyrrolidone as the reaction solvent which is easily filtered from the product for recovery and recyclization to the reaction zone. N-methylpyrrolidone also exhibits an inherent neutralizing effect in the reaction and eliminates contamination of product with carcinogens, such as that which results from dioxane solvent solutions. Further, N-methylpyrrolidone, possesses good solubility properties for this reaction.

As illustrative of the present invention, resorcinol is contacted with a benzotrihalide, preferably benzotrichloride, in an aqueous solution of N-methylpyrrolidone under mild reaction conditions including a temperature of between about 35° to about 100° C., under atmospheric pressure for a period of from about 1 to about 10 hours. In the above reaction, the mole ratio of resorcinol to benzotrihalide introduced into the reaction zone may be varied, but for practical considerations a mole ratio of about 1:1 or a slight excess of the benzotrihalide is preferred. However, it is understood that a ratio of between about 1:2 and about 1.5:1 is acceptable, particularly when it is desirable to recycle excess reactant.

The concentration of N-methyl-2-pyrrolidone in water used in the present process is generally between about 10 wt. % and about 90 wt. %, preferably between about 20 wt. % and about 50 wt. % and comprises from about 5% to about 50%, preferably 10 to 30% by wt. of the reaction mixture.

In operating the reaction, it is beneficial to dissolve the resorcinol in the aqueous N-methylpyrrolidone solution and to gradually add the benzotrihalide to the aqueous mixture with agitation. However, all components of the reaction mixture can be introduced simultaneously or the resorcinol can be added to a benzotrihalide solution in the reaction zone with adequate agitation. After the reaction is complete, the reaction mixture, containing solid product, is allowed to cool and is filtered to remove aqueous N-methylpyrrolidone. The uncontaminated filtrate can be recycled to the reaction zone if desired. The resulting filter cake is then elutriated in water and optionally rinsed with an organic solvent such as toluene, benzene, chlorobenzene, dichloromethane, cyclohexane, or the like to remove small amounts of organic by-products before purification. The crude product is subjected to vacuum distillation under a pressure of not more than 160 mm Hg and product is distilled off at above its melting point. It is preferable to conduct the vacuum distillation at a temperature of at least 150° C. when 1,2-dihydroxybenzophenone is the desired product. The distillate, upon cooling, provides 2,4-dihydroxybenzophenone in at least 90% overall yield and in white crystalline form which shows no coloration upon aging.

According to this invention the crude product mixture can be filtered prior to vacuum distillation as described above or the entire crude product mixture from the reactor can be directly subjected to vacuum distillation at the critical temperature and pressure ranges set forth above. The later operation permits separation of all by-products, solvent and unconverted reactants from product in a single operation which greatly simplifies recovery of pure dihydroxybenzophenone.

Among the prominent uses of 2,4-dihydroxybenzophenone as ultraviolet light stabilizers, are those involving utilization in cosmetic formulations. Also, the compound is used to stabilize resinous, polymeric and plastic materials or as intermediates for other light stabilizers. Accordingly, it is of utmost importance to recover product in a highly purified state which is stable upon aging. The present process achieves these goals while simultaneously providing a simplified and commercially feasible process of manufacture.

Although the vacuum distillation purification in the above disclosure is specifically directed to the reaction of resorcinol with a benzotrihalide, it is to be understood that this purification can be applied in the same manner to any of the crude product mixtures resulting from well known syntheses for 2,4-dihydroxybenzophenone and its substituted derivatives.* Accordingly, the present vacuum distillation can be advantageously used on the crude product obtained from reactions of resorcinol and its derivatives with benzotrihalide and its derivatives, all of which produce 6-hydroxy-9-phenyl-3H-xanthen-3-one contaminant in varying amounts. The present vacuum distillation is also beneficial for the purification of crude product resulting from the reaction of resorcinol with benzoyl chloride, benzoic acid, benzonitrile or phthalic anhydride which reactions are also well known for the production of dihydroxybenzophenone in a crude contaminated state.

* For example, see U.S. Pat. No. 3,769,349, column 2 incorporated herein by reference.

Having described the invention, reference is now had to the following examples, which set forth preferred embodiments of the invention. It is to be understood, however, that the invention is not limited to the examples but that its scope includes aspects, modifications and variations which will become apparent from the aforegoing disclosure.

EXAMPLE 1

PREPARATION OF 2,4-DIHYDROXYBENZOPHENONE

A. REACTION

A 5-liter glass flask, containing 388.5 g (3.53 moles) of resorcinol, 678 g of water and 333 ml of N-methyl-2-pyrrolidone, was heated to 40° C. in a water bath. Benzotrichloride 764.7 g (3.9 moles) was added to the mixture over a period of 3.5 hours with stirring. The resulting mixture was stirred for an additional 3 hours at 45°-50° C., after which it was allowed to cool to room temperature and then filtered. The crude product, a golden yellow cake was transferred to a 4 liter beaker where it was soaked for 1 hour in 500 ml of water and refiltered. The resulting golden yellow cake was again soaked for 1 hour in 500 ml of water and filtered a third time. The filter cake was then rinsed with 250 ml of toluene, filtered and dried for 2 days in a vacuum oven at 75°-80° C. until constant weight was obtained. The product (725 g) was recovered in 96% yield.

B. PRODUCT PURIFICATION

Of the above solid, golden yellow product, 71 g was vacuum distilled at 180°-185° C. under 1 mm Hg in a Kugelroh pot to provide 65.5 g of white crystals having a melting point at 145°-146° C.

EXAMPLE 2

A 5-liter glass flask, containing 388.5 g (3.53 moles) of resorcinol, 678 g of water and 333 ml of methanol, was heated to 40°-45° C. in a water bath. Benzotrichloride 764.7 g (3.9 moles) was added to the mixture over a period of 2 hours with stirring. The resulting mixture was stirred for an additional 3 hours at 50° C., after which it was allowed to cool to room temperature and then filtered. The crude product, a golden yellow cake was transferred to a 4 liter beaker where it was soaked for 1 hour in 500 ml of water and refiltered. The resulting golden yellow cake was again soaked for 1 hr. in 500 ml of water and filtered a third time. The filter cake was then rinsed with 250 ml of toluene, filtered and dried for 2 days in a vacuum oven at 75°-80° C. until constant weight was obtained. The product (682 g) was recovered in 90% yield.

The above solid, golden yellow product, was vacuum distilled at 180°-185° C. under 1 mm Hg in a Kugelroh pot to provide white crystals having a melting point at 145°-146° C.

EXAMPLE 3

The reaction of resorcinol and benzotrichloride as described in Example 1 is repeated, except that upon completion of the reaction the entire reaction mixture is not washed but is subjected to vacuum distillation under 0.1 mm Hg at 155°-165° C. White crystalline product is again obtained.

What is claimed is:

1. In a process for the synthesis of a dihydroxybenzophenone from the reaction between a resorcinol and a benzoic coreactant in an aqueous reaction medium, wherein the crude dihydroxybenzophenone product is obtained in the reaction zone mixture as a solid the improvement which comprises subjecting the crude dihydroxybenzophenone product to vacuum distillation under a pressure not exceeding 160 mm Hg at a temperature between 120° C. and about 350° C. to distill off a dihydroxybenzophenone product.

2. The process of claim 1 wherein resorcinol is reacted with a benzotrihalide to produce 2,4-dihydroxybenzophenone and wherein the crude 2,4-dihydroxybenzophenone product is subjected to vacuum distillation under a pressure of from about 0.001 mm Hg to about 60 mm Hg at a temperature between about 150° C. and about 250° C.

3. The process of claim 1 wherein the crude dihydroxybenzophenone product in the reaction zone mixture is filtered to separate the crude product from the reaction medium prior to vacuum distillation.

4. The process of claim 1 wherein the entire mixture from the reaction zone including said crude dihydroxybenzophenone product is directly subjected to vacuum distillation.

5. The process of claim 2 wherein resorcinol is reacted with a benzotrichloride.

6. In a process for the synthesis of 2,4-dihydroxybenzophenone from the reaction of resorcinol with benzotrihalide in an aqueous reaction medium wherein the crude 2,4-dihydroxybenzophenone product is obtained in the reaction zone mixture as a solid, the improvement which comprises conducting the reaction in the presence of an aqueous solution of N-methylpyrrolidone as the reaction medium.

7. The process of claim 6 wherein the concentration of N-methylpyrrolidone in aqueous solution is between about 10% and about 90% by weight.

8. The process of claim 7 wherein the concentration of N-methylpyrrolidone in aqueous solution is between about 20% and about 50% by weight.

9. The process of claim 6 wherein the N-methylpyrrolidone solution comprises from about 5% to about 50% by weight of the reaction mixture.

10. The process of claim 9 wherein the N-methylpyrrolidone solution comprises from about 10% to about 30% by weight of the reaction mixture.

11. The process of claim 6 wherein the crude 2,4-dihydroxybenzophenone product is vacuum distilled under a pressure of from about 0.001 mm to about 60 mm Hg at a temperature between 150° C. and about 250° C. to distill off a dihydroxybenzophenone product.

12. The process of claim 11 wherein the reaction zone mixture is filtered to separate the solid crude 2,4-dihydroxybenzophenone product from the reaction medium prior to vacuum distillation.

13. The process of claim 11 wherein the entire mixture from the reaction zone including said crude dihydroxybenzophenone product is directly subjected to vacuum distillation.

* * * * *